United States Patent
Martin et al.

(10) Patent No.: US 6,489,004 B1
(45) Date of Patent: Dec. 3, 2002

(54) HOOK AND LOOP FASTENER HAVING AN INCREASED COEFFICIENT OF FRICTION

(75) Inventors: Timothy R. Martin, Alpharetta, GA (US); Alexander J. Neeb, Alpharetta, GA (US); Richard J. Schmidt, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 30 days.

(21) Appl. No.: 09/705,512

(22) Filed: Nov. 3, 2000

(51) Int. Cl.[7] .................................................. A44B 18/00
(52) U.S. Cl. .............................. 428/100; 428/99; 24/451
(58) Field of Search ..................... 428/99, 100; 24/451, 24/442

(56) References Cited

U.S. PATENT DOCUMENTS

| | | |
|---|---|---|
| 4,680,838 A | 7/1987 | Astl |
| 4,811,468 A | 3/1989 | Yamada |
| 4,875,259 A | 10/1989 | Appledorn |
| 4,946,527 A | 8/1990 | Battrell |
| 5,201,101 A | 4/1993 | Rouser et al. |
| 5,657,516 A | 8/1997 | Berg et al. |
| 6,043,168 A | 3/2000 | Colman et al. .............. 442/118 |
| 6,077,255 A | 6/2000 | Hunter et al. |

FOREIGN PATENT DOCUMENTS

| | | |
|---|---|---|
| DE | 197 32 552 A1 | 2/1999 |
| EP | 0 418 954 | 3/1991 |
| EP | 0 476 992 | 7/1995 |
| EP | 0 862 868 | 9/1998 |
| EP | 0 862 868 A1 | 9/1998 |
| EP | 0 893 075 A2 | 1/1999 |
| EP | 0 894 448 | 2/1999 |
| WO | 96/25905 | 8/1996 |
| WO | 98/10728 | 3/1998 |

*Primary Examiner*—Alexander S. Thomas
(74) *Attorney, Agent, or Firm*—Pauley Petersen Kinne & Erickson

(57) ABSTRACT

A hook and loop fastener having an increased coefficient of friction compared to conventional nonwoven hook and loop systems. The increased coefficient of friction strengthens engagement between a hook component and a loop component, both when the hooks and loops are engaged, and even when the hooks and loops are not engaged but merely in contact with one another. The coefficient of friction can be increased by adding tackifiers in the hook forming process and/or in the loop forming process, or by extruding multi-component fibers using a fiber type that enhances strength and a fiber that has less strength but has a higher coefficient of friction, or by using fibers of various cross-sectional shapes, or by processing surface bloom additives into the hook and/or loop structures.

14 Claims, 2 Drawing Sheets

HOOK AND LOOP FASTENER HAVING AN INCREASED COEFFICIENT OF FRICTION

BACKGROUND OF THE INVENTION

This invention is directed to a hook and loop fastener. A number of fastening systems, such as diaper fastening systems, incorporate a hook and loop system for easy fastening and release. The hook component typically includes a flat plastic sheet laminate with a number of protruding hooks that engage (i.e., mesh or interlock) with a number of loops protruding from a corresponding loop component. While many of the individual hooks engage with individual loops, many of the individual hooks and the individual loops are merely in contact with one another with no engagement between them. These non-engaged hooks and loops neither help nor hinder overall fastening strength between the hook component and the loop component.

There is a need or desire for a hook and loop fastener wherein all or most of the individual hooks and loops (including those which touch but are not engaged) contribute to the fastening strength between the hook component and the loop component.

SUMMARY OF THE INVENTION

The present invention is directed to a hook and loop fastener whose components have an increased coefficient of friction compared to conventional nonwoven hook and loop fasteners. By increasing the coefficient of friction, the fastening performance of the hook and loop fastener is increased by increasing the forces required to separate both engaged and contacting (but not engaged) hooks and loops. Essentially, the hook fastener and the loop fastener remain engaged or in contact for a longer period of time than conventional hook and loop fasteners due to the increased coefficient of friction which requires a greater force of separation.

In one embodiment of the invention, the coefficient of friction can be increased by adding a tackifier to the hook and/or loop components, for instance, in the hook forming process and/or the loop forming process. In another embodiment, a friction modifier can be painted onto the surface of hooks and/or loops already formed. In another embodiment of the invention, multi-component fibers can be extruded to form a loop component. The multi-component fibers can include a fiber type that enhances strength and a fiber type that has less strength but has a higher coefficient of friction. In yet another embodiment of the invention, multi-shaped, multi-lobal, or irregular-shaped fibers are used to increase the total friction by increasing the contact surface area and providing edges. In still another embodiment of the invention, surface bloom additives can be processed into the hook and/or loop structures in such a way as to increase the coefficient of friction of the fastener after blooming is complete.

Any of these improvements to the hook and loop fastener, or a combination of these improvements, result in a hook and loop fastener having increased friction between the hooks and loops, such that the individual hooks and loops facilitate engagement between the hook component and the loop component, even between non-engaged hooks and loops in contact with one another.

With the foregoing in mind, it is a feature and advantage of the invention to provide a hook and loop fastener having increased friction between the hooks and loops.

DEFINITIONS

Figure 1:
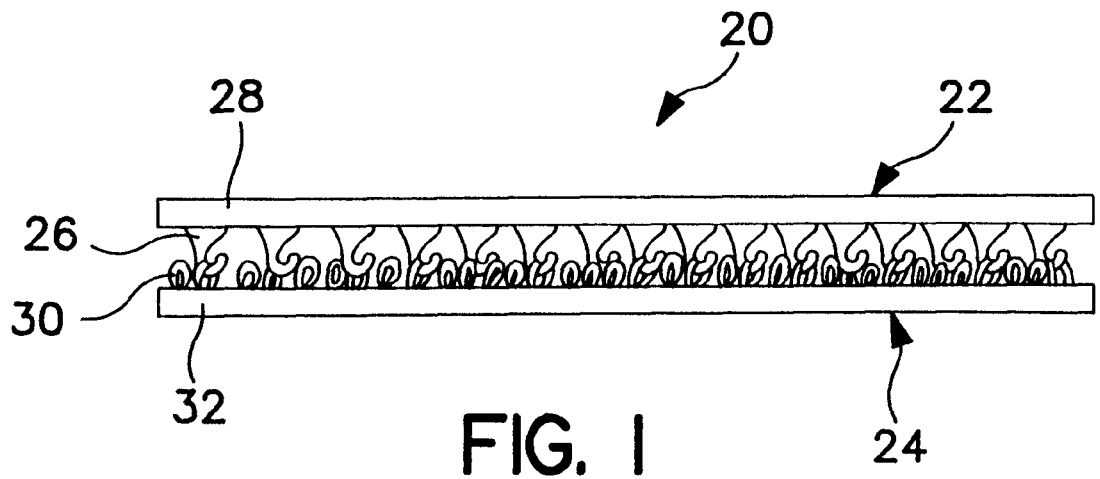
FIG. 1 is a front view of a hook component and a loop component engaged with one another.

Within the context of this specification, each term or phrase below will include the following meaning or meanings.

"Bicomponent fibers" refer to fibers which have been formed from at least two polymers extruded from separate extruders but spun together to form one fiber.

"Friction" refers to a force that resists relative motion between two bodies in contact. The term "coefficient of friction" refers to the ratio of the magnitude of the force of friction to the magnitude of the normal force applied to an object being moved along a surface. An increased coefficient of friction enables two bodies to stay in contact more easily than a lower coefficient of friction, thus, it is more difficult to separate two bodies having an increased coefficient of friction than it is to separate two bodies having a lower coefficient of friction.

"Medical garment" includes medical (i.e., protective and/or surgical) gowns, caps, gloves, drapes, face masks, blood pressure cuffs, bandages and the like.

"Peel force" refers to a force that tends to pull two adjoining bodies away from one another in opposite directions generally perpendicular to a plane in which the bodies are joined. Peel force may also be referred to as "fastening strength."

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Shear force" refers to a force that tends to produce an opposite but parallel sliding motion between two bodies' planes.

"Surface bloom" refers to a process wherein a substance is added to a material and migrates from one region of the material to another region, particularly to a surface region. The term "surface bloom additive" refers to the substance that migrates between regions in the material.

"Tackifier" refers to a resin having a slightly adhesive, sticky or gummy feel. Tackifiers can be used to coat solid materials to create a tacky surface on the solid. Alternatively, tackifiers can be blended with other polymers to create a material having a tacky surface. The resulting tacky surface creates greater friction between the coated solid or blended material and virtually any other surface, compared to the friction between the uncoated solid or unblended polymers and other surfaces.

"Thermoplastic" describes a material that softens when exposed to heat and which substantially returns to a non-softened condition when cooled to room temperature.

These terms may be defined with additional language in the remaining portions of the specification.

DETAILED DESCRIPTION OF THE PRESENTLY PREFERRED EMBODIMENTS

The present invention is directed to a hook and loop fastener having increased friction between the hooks and loops, compared to conventional nonwoven hook and loop fasteners. Each of the embodiments of the invention result in an increased coefficient of friction between a hook component and a loop component, and/or an increased area of contact between the hooks and loops.

This hook and loop fastener is particularly suitable for use in fastening systems on disposable absorbent articles. Examples of such suitable articles include diapers, training pants, feminine hygiene products, incontinence products, other personal care or health care garments, including medical garments, or the like.

As shown in FIG. 1, a fastening system 20 including a hook component 22 and a loop component 24 can be brought together to be releasably attached, or releasably engaged, to one another. The hook component 22 has a number of individual hooks 26 protruding generally perpendicularly from a hook backing material 28. Similarly, the loop component 24 has a number of individual loops 30 protruding generally perpendicularly from a loop backing material 32. The individual hooks 26 and the individual loops 30, when brought into contact with one another, engage with one another, with the hooks 26 latching onto the loops 30, until forcibly separated, thereby pulling the hooks 26 out of the loops 30.

As illustrated in FIG. 1, not every hook 26 and every loop 30 engages with a corresponding loop 30 or hook 26. Typically, enough hooks 26 and loops 30 engage with one another to maintain fastening between the hook component 22 and the loop component 24. By increasing the coefficient of friction and/or total friction within the hook and loop fastener 20, between the hooks 26 and loops 30, peel and shear forces within the fastener 20 are increased, thereby requiring greater peel and shear forces acting on the fastener 20 to separate the hook component 22 from the loop component 24. With an increased coefficient of friction, even non-engaged hooks 26 and loops 30 in contact with one another provide a degree of peel force and shear force, and may contribute to the fastening strength as well.

Figure 2:
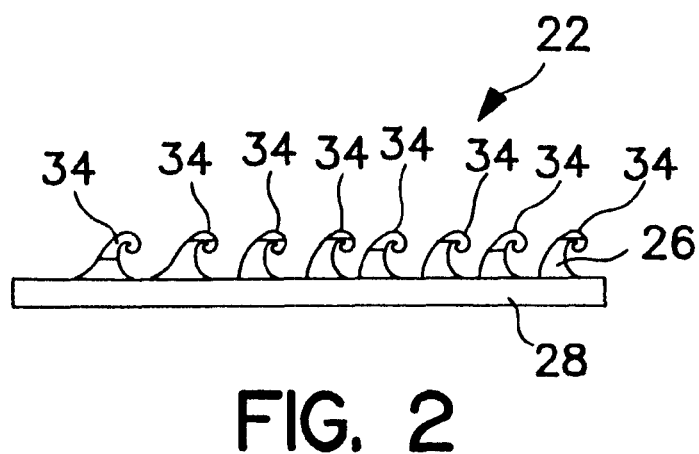
FIG. 2 is a side view of a hook component having a tackifier on the hooks.

In one embodiment, shown in FIG. 2, the hooks 26 on the hook component 22 are at least partially coated with a tackifier 34. The tackifier 34 can either be applied to the surfaces of the hooks 26 or can be blended with the hook material during the hook forming process, whereupon some of the tackifier 34 will be present at the hook surfaces or migrate to the hook surfaces. The tackifier 34 gives the hooks 26 a slightly adhesive, sticky or gummy feel. Thus, when the hooks 26 come in contact with the loops 30, the friction between the hook component 22 and the loop component 24 is increased, thereby increasing the amount of shear force and/or peel force necessary to separate the hook component 22 from the loop component 24. The peel force is increased by the added friction because, as shown in FIG. 1, the individual hooks 26 and individual loops 30 are positioned so as to shear one another when the hook component 22 and loop component 24 are peeled apart.

Figure 3:
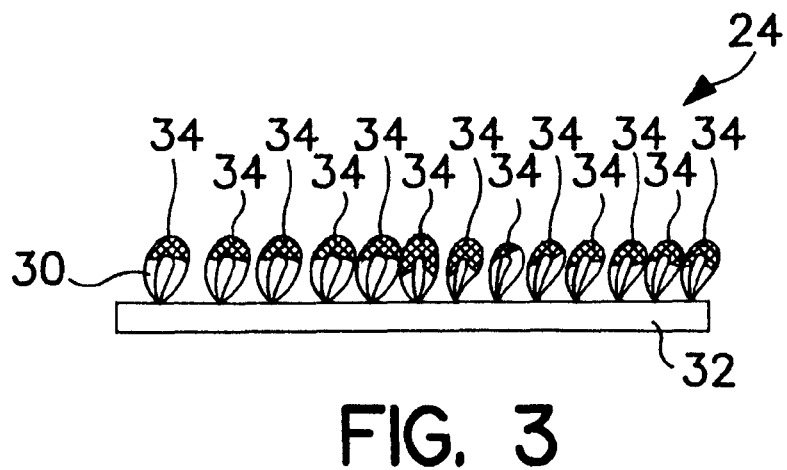
FIG. 3 is a side view of a loop component having a tackifier on the loops.

In another embodiment, shown in FIG. 3, the loops 30 on the loop component 24 are at least partially coated with a tackifier 34. The tackifier 34 can either be used to coat the loops 30 or can be added to the loop material during the loop forming process. Similar to the previous embodiment, the tackifier 34 gives the loops 30 a slightly adhesive, sticky or gummy feel, thereby increasing the friction between the hook component 22 and the loop component 24. Both the hook component 22 and the loop component 24 can include tackifiers 34 on the hooks 26 and loops 30, or merely just the hook component 22 or just the loop component 24 may include the tackifier 34.

The tackifier 34 can include any suitable resin that lends tackiness, or slight stickiness, to the hook component 22 and/or loop component 24. Examples of suitable resins include polyethylene elastomers, syndiotactic polypropylene, polybutylene, blends of rubber and polypropylene, styrene block copolymers, or combinations thereof. One example of a suitable resin is REGALREZ®, manufactured by Hercules Corporation, Wilmington, Del. The tackifier 34 may be a material which can be painted, spray-coated or otherwise externally applied to the hooks 26 and loops 30, or a material which can be internally applied by blending with the hook and/or loop polymer(s).

Figure 4:
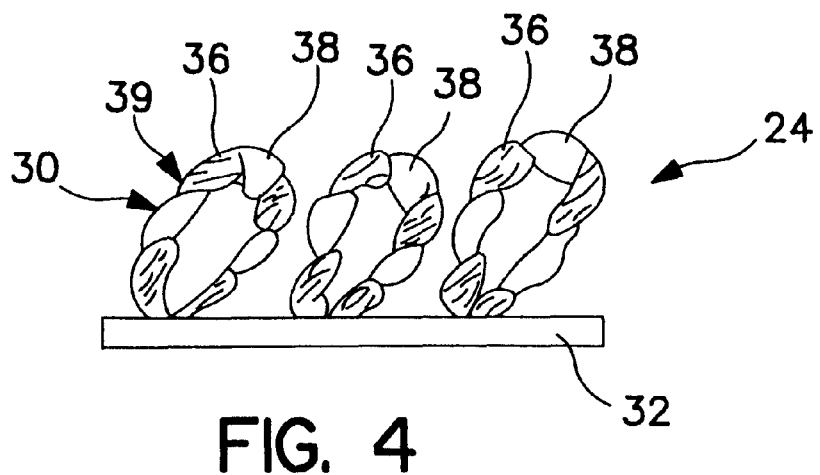
FIG. 4 is a side view of a loop component having loops made of multi-component fibers.

In another embodiment of the invention, shown in FIG. 4, the coefficient of friction of a nonwoven loop component 24 is increased by using extruded multi-component 36, 38 fibers 39 to make individual loops 30 protruding from the loop backing 32. A combination of fiber components suitably includes a first fiber component 36 that enhances strength, such as a thermoplastic polymer selected from polyamides, polyesters, polyolefins (e.g. polypropylene or polyethylene) or another suitable material. A second suitable fiber component 38 has less strength than the first fiber component 36, but has a higher coefficient of friction. Suitable examples of the second fiber component 38 include any of the same types of fibers suitable for the first fiber component 36, as long as the type of fiber selected for use as the first fiber component 36 is not the same as the type of fiber selected for use as the second fiber component 38.

Bicomponent fibers can also be used. The configuration of bicomponent fibers may be, for example, a "sheath-core" arrangement, wherein one polymer is surrounded by another. In particular, the first fiber component 36, the strength component, can be used as the core and the second fiber component 38, the friction component, can be used as the sheath. Other bicomponent arrangements include a "side-by-side" arrangement, or an "islands-in-the-sea" arrangement, both of which are known in the art.

Figure 5:
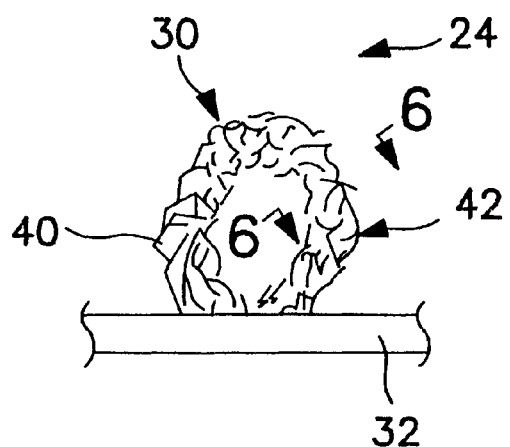
FIG. 5 is a side view of an individual loop made of multi-shaped fibers.
Figure 6:
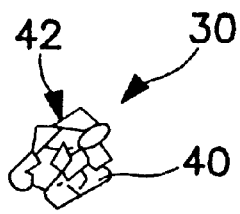
FIG. 6 is cross-sectional view of a loop made of multi-shaped fibers, taken along line 6—6 in FIG. 5.

In yet another embodiment of the invention, shown in FIGS. 5 and 6, multi-shaped or irregular-shaped fibers 40 are used in the loop component 24 to increase the coefficient of friction by affecting the surface area and the edge effect on the loops 30. More specifically, FIG. 6 shows the cross-section of the loop 30 in FIG. 5. The loop 30 in this embodiment has a non-smooth outer surface 42, which creates a higher coefficient of friction compared to a loop having a smooth outer surface. By having a non-smooth outer surface 42, the surface area of the outer surface is increased and a number of edges are created about the outer surface. These edges increase the amount of friction between the loop 30 and a corresponding hook 26, either while engaged or merely in contact with one another, by creating a claw-like effect by which the edges of the loop 30 can dig into the hook 26. For example, each of the fibers 40 in the loop 30 can have a unique and/or irregular shape, or at least two different types of fiber shapes can be included in the loop 30, suitably at least three different types of fiber shapes can be included in the loop. The fiber shapes, determined by the cross-sectional shapes of the fibers 42, can be elliptical, three-sided, four-sided, or generally any other shape, either geometrical or irregular.

In still another embodiment of the invention, surfactant blooming technology can be used to process a surface bloom additive into fibers of the hook and/or loop structures in such a way as to increase the coefficient of friction of the fastener 20 after blooming is complete. Surfactant blooming technology is taught, for example, in U.S. Pat. No. 6,043,168 issued to Colman, et al., hereby incorporated by reference. More particularly, the surfactant blooming process can be carried out by using a treatment system of at least one internal surface bloom additive and/or at least one topical surface additive. The internal surface bloom additive is blended with the hook and/or loop material during the hook and/or loop forming process. The internal surface bloom additive is a substance that remains amorphous in the fibers, such as syndiotactic polypropylene or polybutylene, for example. In carrying out the blooming process, the internal surface bloom additive is added to a polyolefin resin, which is then spun into the fibers of the hook and/or loop material.

The topical surface additive is applied to the surfaces of the hooks and/or loops, and can include any of the same substances as the internal surface bloom additive.

In each of the embodiments, the individual loops 30 of the loop component 24 can be needled, stitched or otherwise projected through the loop backing material 32, which can suitably be made from a nonwoven material. In addition to the processing improvements disclosed herein, the individual loops 30 can suitably be made from a fibrous nonwoven web such as a spunbond nonwoven web, or a staple fiber carded web. Alternatively, the individual loops 30 can be made of yarn or tow. Once the loops 30 have been formed, fibers forming the loops can be anchored in place by bonding the fibers to the loop backing material 32 with heat and/or adhesives or any other suitable means.

The loops 30 are not necessarily of a uniform height, but preferably have a height in a range of from about 0.00254 cm to about 0.19 cm, or from about 0.0381 cm to about 0.0762 cm. The loop backing 32 generally has a thickness in a range of between about 0.025 millimeter (mm) and about 5 mm, suitably between about 0.4 mm and about 2 mm. The density of the loops 30 on the loop backing 32 is largely dependent on the type of material used, and can range from about 16 to about 620 loops per square centimeter, or from about 124 to about 388 loops per square centimeter, or from about 155 to about 310 loops per square centimeter.

In each of the embodiments, the individual hooks 26 of the hook component 22 typically have a base portion that extends roughly perpendicularly from the hook backing 28 and a free end extending from the base portion that is curved or angled to enable engagement with a corresponding loop 30 on the loop component 24. Virtually any hook shape can be used with this invention. For example, the individual hooks 26 can have J-shaped free ends or flat free ends. The hooks 26 are typically co-formed with the hook backing material 28. A co-extrusion process can be employed to form the individual hooks 26 and the backing material 28 from various polymers in the same process.

Suitable hook components 22 generally have between about 16 and about 620 hooks per square centimeter, or between about 124 and about 388 hooks per square centimeter, or between about 155 and about 310 hooks per square centimeter. The hooks 26 suitably have a height of from about 0.00254 centimeter (cm) to about 0.19 cm, or from about 0.0381 cm to about 0.0762 cm. In addition to the processing improvements disclosed herein, the hooks 26 are suitably molded or extruded from a thermoplastic polymer selected from polyamides, polyesters, polyolefins (e.g. polypropylene or polyethylene) or another suitable material that contributes strength and/or friction to the fastening system 20. Likewise, the hook backing material 28 can be made of any of these or any other suitable materials. The hook backing material 28 generally has a thickness in a range of between about 0.5 millimeter (mm) and about 5 mm, suitably in a range of between about 0.8 mm and 3 mm, with a basis weight in a range of from about 20 grams per square meter to about 70 grams per square meter.

A fastening system 20 having an increased coefficient of friction results from any of the disclosed embodiments, or a combination of the disclosed embodiments. The fastening system 20 of the invention suitably has a kinetic coefficient of friction at least 25% greater than the same fastening system without any coefficient of friction modifiers. More suitably, the kinetic coefficient of friction with the friction modifiers is between about 25% and about 50% greater than the same fastening system without any coefficient of friction modifiers, as shown in the example below.

EXAMPLE

In this example, a piece of spunbond polypropylene was used as a control and the kinetic coefficient of friction of the control was compared to the kinetic coefficient of friction of six samples each including a coefficient of friction modifier. The results are shown in Table 1. The average increase in kinetic coefficient of friction in the samples having a coefficient of friction modifier was 42%. The kinetic coefficient of friction was measured using the test procedure described below.

TABLE 1

Comparison of Kinetic Coefficients of Friction

| Sample | Load Peak (grams) | Kinetic Co-efficient of Friction | Increase in Kinetic Coefficient of Friction Compared to Control |
|---|---|---|---|
| 100% polypropylene (control) | 74 | 0.26 | — |
| 0.6 osy, 40% polypropylene, 60% metallocene polyethylene | 80 | 0.38 | 46% |
| 0.6 osy, 55% polypropylene, 45% metallocene polyethylene | 87 | 0.38 | 46% |
| 0.6 osy, 70% polypropylene, 30% ARNITEL ® EM400* | 82 | 0.34 | 31% |
| 1.0 osy, 40% polypropylene, 60% metallocene polyethylene | 84 | 0.34 | 31% |
| 1.0 osy, 55% polypropylene, 45% metallocene polyethylene | 83 | 0.35 | 35% |

TABLE 1-continued

Comparison of Kinetic Coefficients of Friction

| Sample | Load Peak (grams) | Kinetic Co-efficient of Friction | Increase in Kinetic Coefficient of Friction Compared to Control |
|---|---|---|---|
| 1.0 osy, 70% polypropylene, 30% ARNITEL ® EM400* | 96 | 0.41 | 58% |

*a copolyester elastomer available from DSM Engineering Plastics of Evansville, Indiana

Standard Test Method for Kinetic Coefficients of Friction of Plastic Film and Sheeting, Astm D-1894-78

This test method covers determination of the coefficient of sliding friction of plastic film and sheeting when sliding over itself or other substances at specified test conditions.

Apparatus used to carry out the test method includes a sled made of a metal block 63.5 mm (2.5 inches) square by approximately 6 mm (0.25 inch) thick with a suitable eye screw fastened in one end. In addition, a polished plastic, wood, or metal sheet, approximately 150 by 300 by 1 mm (6 by 12 by 0.040 inch) is used as a plane. A smooth, flat piece of glass may cover the upper surface of the plane, thereby providing a smooth support for the specimen. Other materials include scissors or a cutter suitable for cutting specimens to the desired dimensions, adhesive tape such as cellophane or pressure-sensitive tape, and double-faced adhesive tape. Additional materials include a nylon monofilament, having a 0.33±0.05 mm (0.013±0.002 inch) diameter and capable of supporting a 3.6 kg (8 pound) load, low-friction pulleys such as a phenolic type pulley mounted in hardened steel cone bearings on a metal fork, or a ball-bearing type pulley may be used, and a force-measuring device capable of measuring the frictional force to ±5% of its value, for example a spring gage, a universal testing machine or a strain gage may be used. Other equipment includes a supporting base. A smooth wood or metal base approximately 200 by 380 mm (8 by 15 inches) is necessary to support the plane. The supporting base may be a simple rectangular box. A driving or pulling device for the sled or plane is also needed. The plane may be pulled by a driven pair of rubber-coated rolls not less than 200 mm (8 inches) long, capable of maintaining a uniform surface speed of 150±30 mm/min (0.5±0.1 ft/min) by the crosshead of a universal testing machine, or a worm drive driven with a synchronous motor. A constant-speed chain drive system can also be used. A power-operated source may be used for pulling the sled over the horizontally-mounted specimen at a uniform speed of 150±30 mm/min (0.5±0.1 ft/min).

The test specimen that is to be attached to the plane should be cut approximately 250 mm (10 inches) in the machine direction and 130 mm (5 inches) in the transverse direction when such extrusion directions exist and are identifiable. A film specimen, having a nominal thickness of not greater than 0.254 mm, should be cut approximately 120 mm (4.5 inches) square. A sheeting specimen, greater than 0.254 mm nominal thickness, should be cut 63.5 mm (2.5 inches) square.

The test method is carried out by taping the 250 by 130 mm (10 by 5 inch) film or sheet specimen to a plane with the machine direction of the specimen in the 250-mm direction. Smooth the film specimen to eliminate wrinkles if necessary, taking care not to alter the specimen surface through finger oils, etc. For film specimens, tape the edges of the 120 mm (4.5 inch) square film specimen to the back of the sled, using adhesive tape and pulling the specimen tight to eliminate wrinkles without stretching it. For sheet specimens, tape the 63.5 mm (2.5 inch) square sheet specimen or second substrate to the sled face with double-faced tape. Keep the machine direction of the specimen parallel to the length of the sled (where such direction exists and is identifiable).

Next, attach the specimen-covered sled through its eye screw to the nylon filament. If a universal testing machine is used, pass the filament through the pulley(s) and upward to the bottom of the load-sensing device and attach securely. If a spring gage is used, securely attach the filament to it. The nylon filament shall be of sufficient length to allow maximum sled or plane travel. With some slack in the nylon filament, lightly place the sled in position on the horizontal plane. The positioning of the sled shall be such that the length of the sled, the adjacent length of nylon filament, and the long dimension (machine direction) of the plane-mounted specimen are parallel.

Start the driving mechanism (which has been adjusted previously to provide a speed of 150±30 mm/min (0.5±0.1 ft/min)). As a result of the frictional force between the contacting surfaces, no immediate relative motion may take place between the sled and the moving plane until the pull on the sled is equal to, or exceeds the static frictional force acting at the contact surfaces. Record the visual average reading during a run of approximately 130 mm (5 inches) while the surfaces are sliding uniformly over one another. This is equivalent to the kinetic force required to sustain motion between the surfaces and normally is lower than the static force required to initiate motion. After the sled has traveled over 130 mm (5 inches) stop the apparatus and return to the starting position.

If a strain gage and load-displacement recorder are used, either draw the best straight line midway between the maximum points and minimum points shown on the chart while the sled was in motion, or obtain the average load by integration of the recorder trace. The mean load is the kinetic friction force required to sustain motion on the sled.

Remove the film or sheeting specimen from the sled and the horizontal plane. The apparatus is now ready for the next set of specimens. A new set of specimens shall be used for each run.

Calculate the kinetic coefficient of friction, $\mu_k$, as follows:

$$\mu_k = A_k/B$$

where:

$A_k$=average scale reading obtained during uniform sliding of the film surfaces, and B=sled weight.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A hook and loop fastener comprising a hook component and a loop component;

the loop component including a loop backing and a plurality of loops protruding from it; and the hook component including a hook backing, a plurality of hooks protruding from it, and a coefficient of friction modifier comprising a tackifier, wherein the tackifier is blended with a polymer from which the plurality of hooks is made.

2. The hook and loop fastener of claim 1, wherein the hook and loop fastener has a kinetic coefficient of friction at least 25% greater than the same type of hook and loop fastener without the coefficient of friction modifier.

3. The hook and loop fastener of claim 1, wherein the hook and loop fastener has a kinetic coefficient of friction between about 25% and about 50% greater than the same type of hook and loop fastener without the coefficient of friction modifier.

4. The hook and loop fastener of claim 1, wherein the tackifier comprises a resin selected from the group consisting of polyethylene elastomers, syndiotactic polypropylene, polybutylene, blends of rubber and polypropylene, styrene block copolymers, and combinations thereof.

5. A hook and loop fastener comprising a hook component and a loop component;

the hook component including a hook backing and a plurality of hooks protruding from it; and the loop component including a loop backing, a plurality of loops protruding from it, and a coefficient of friction modifier comprising a tackifier, wherein the tackifier is blended with a polymer from which the plurality of loops is made.

6. The hook and loop fastener of claim 5, wherein the hook and loop fastener has a kinetic coefficient of friction at least 25% greater than the same type of hook and loop fastener without the coefficient of friction modifier.

7. The hook and loop fastener of claim 5, wherein the hook and loop fastener has a kinetic coefficient of friction between about 25% and about 50% greater than the same type of hook and loop fastener without the coefficient of friction modifier.

8. The hook and loop fastener of claim 5, wherein the tackifier comprises a resin selected from the group consisting of polyethylene elastomers, syndiotactic polypropylene, polybutylene, blends of rubber and polypropylene, styrene block copolymers, and combinations thereof.

9. A hook and loop fastener comprising a hook component and a loop component;

the hook component including a hook backing, a plurality of hooks protruding from it, and a first coefficient of friction modifier comprising a tackifier, wherein the tackifier is blended with a polymer from which the plurality of hooks is made; and the loop component including a loop backing, a plurality of loops protruding from it, and a second coefficient of friction modifier.

10. The hook and loop fastener of claim 9, wherein the hook and loop fastener has a kinetic coefficient of friction at least 25% greater than the same type of hook and loop fastener without the first coefficient of friction modifier and without the second coefficient of friction modifier.

11. The hook and loop fastener of claim 9, wherein the hook and loop fastener has a kinetic coefficient of friction between about 25% and about 50% greater tan the same type of hook and loop fastener without the first coefficient of friction modifier and without the second coefficient of friction modifier.

12. A hook and loop fastener comprising a hook component and a loop component;

the hook component including a hook backing, a plurality of hooks protruding from it, and a first coefficient of friction modifier; and the loop component including a loop backing, a plurality of loops protruding from it, and a second coefficient of friction modifier comprising a tackifier, wherein the tackifer is blended with a polymer from which the plurality of loops is made.

13. The hook and loop fastener of claim 12, wherein the hook and loop fastener has a kinetic coefficient of friction at least 25% greater than the same type of hook and loop fastener without the first coefficient of function modifier and without the second coefficient of friction modifier.

14. The hook and loop fastener of claim 12, wherein the hook and loop fastener has a kinetic coefficient of friction between about 25% and about 50% greater than the same type of hook and loop fastener without the first coefficient of friction modifier and without the second coefficient of friction modifier.

* * * * *